(12) United States Patent
Bissantz et al.

(10) Patent No.: US 7,501,432 B2
(45) Date of Patent: Mar. 10, 2009

(54) SPIRO-PIPERIDINE DERIVATIVES

(75) Inventors: Caterina Bissantz, Village-Neuf (FR);
Christophe Grundschober, Rodersdorf (CH); Raffaello Masciadri, Basel (CH); Hasane Ratni, Habsheim (FR); Mark Rogers-Evans, Oberwil BL (CH); Patrick Schnider, Bottmingen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/955,440

(22) Filed: Dec. 13, 2007

(65) Prior Publication Data
US 2008/0167333 A1    Jul. 10, 2008

(30) Foreign Application Priority Data
Dec. 22, 2006    (EP) ................... 06127078

(51) Int. Cl.
*A61K 31/438*    (2006.01)
*C07D 221/20*    (2006.01)

(52) U.S. Cl. .................. 514/278; 546/17; 544/124; 514/232.8

(58) Field of Classification Search ............... 514/278, 514/232.8; 546/17; 544/124
See application file for complete search history.

(56) References Cited

FOREIGN PATENT DOCUMENTS

| EP | 722941 | 7/1996 |
|---|---|---|
| WO | WO 94/07496 | 4/1994 |
| WO | WO 99/29696 | 6/1999 |
| WO | WO 01/14376 | 3/2001 |
| WO | WO 02/48152 | 6/2002 |
| WO | WO 03/045385 | 6/2003 |

OTHER PUBLICATIONS

Ebner et al., Eur. J. Neurosci. vol. 15, pp. 384-388 (2002).
Bielsky et al., Neuropsychopharmacology vol. 29, pp. 483-493 (2004).
Michelini et al., Ann. NY Acad. Sci. vol. 897 pp. 198-211 (1999).
Vankerckhoven et al., Eur. J. Pharmacol. vol. 449, Issue 1-2, pp. 135-141 (2002).
Liebsch et al., Regulatory Peptides vol. 59, Issue 2, pp. 229-239 (1995).
Parham et al., J. Org. Chem. vol. 41, pp. 2628-2633 (1976).
Connor et al., J. Med. Chem. vol. 35, pp. 958-965 (1992).
Itoh et al., Organic Process Research & Development vol. 10(4) pp. 822-828 (2006).

*Primary Examiner*—Charanjit S Aulakh
(74) *Attorney, Agent, or Firm*—George W. Johnston; Patricia S. Rocha-Tramaloni; Kimberly J. Prior

(57) ABSTRACT

The present invention is concerned with novel spiro-piperidine derivatives as V1a receptor antagonists, their manufacture, pharmaceutical compositions containing them and their use as medicaments. The active compounds of the present invention are useful in the prevention and/or treatment of anxiety and depressive disorders and other diseases.

In particular, the present invention is concerned with compounds of the general formula (I)

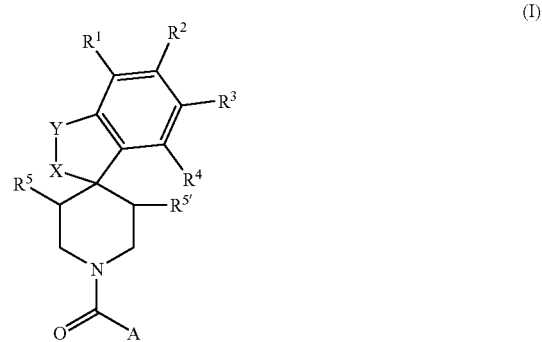

wherein $R^1$ to $R^5$, $R^{5'}$, X, Y and A are as defined in the specification.

22 Claims, No Drawings

SPIRO-PIPERIDINE DERIVATIVES

PRIORITY TO RELATED APPLICATION(S)

This application claims the benefit of European Patent Application No. 06127078.1, filed Dec. 22, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39). The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann N Y Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

SUMMARY OF THE INVENTION

The present invention provides novel spiro-piperidine derivatives as V1a receptor antagonists, their manufacture, pharmaceutical compositions containing them and their use for the treatment of anxiety and depressive disorders and other diseases.

In particular, the present invention provides compounds of formula (I)

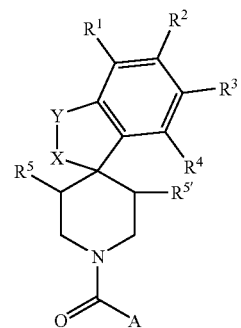

(I)

wherein
X is O and Y is $CH_2$,
X is O and Y is C=O,
X is C=O and Y is $NR^6$,
X—Y is CH=CH,
X—Y is $CH_2$—$CH_2$,
X is C=O and Y is O,
X is $CH_2$ and Y is $NR^6$, or
X is $CH_2$ and Y is O;

A is selected from the group consisting of

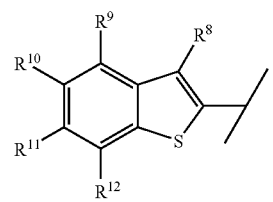

(a)

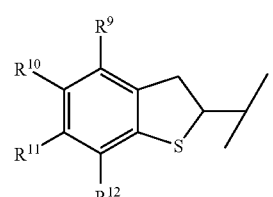

(b)

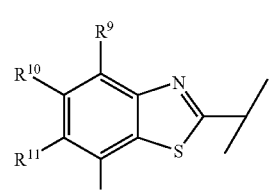

(c)

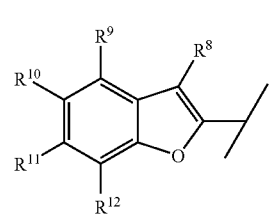

(d)

-continued

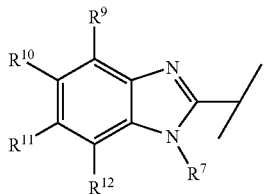
(e)

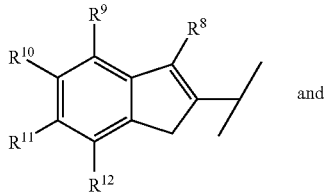
(f)

and

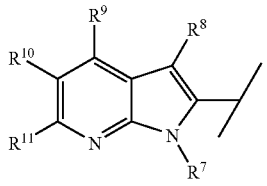
(g)

$R^1$, $R^2$, $R^3$ and $R^4$ are each independently
  hydrogen,
  halo,
  $C_{1-6}$-alkyl, optionally substituted by OH
  halo-$C_{1-6}$-alkyl,
  $C_{1-6}$-alkoxy, optionally substituted by OH, or
  halo-$C_{1-6}$-alkoxy;
$R^5$ and $R^{5'}$ are each independently hydrogen or methyl;
$R^6$ is hydrogen or $C_{1-6}$-alkyl;
$R^7$ is hydrogen,
  $C_{1-6}$-alkyl, optionally substituted by CN or OH, or
  —($C_{1-6}$-alkylene)-C(O)—$NR^aR^b$;
$R^8$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-C(O)$R^f$,
  benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
$R^9$ is hydrogen, halo, $C_{1-6}$-alkyl, or $C_{1-6}$-alkoxy;
$R^{10}$ is hydrogen, halo, $C_{1-6}$-alkyl, halo-$C_{1-6}$-alkyl, $C_{1-6}$-alkoxy, halo-$C_{1-6}$-alkoxy, or —O—$C_{2-10}$-alkenyl;
$R^{11}$ is hydrogen, halo, $C_{1-6}$-alkyl, or $C_{1-6}$-alkoxy;
or $R^{10}$ and $R^{11}$ are bound together to form a ring with the benzo moiety, wherein
  —$R^{10}$—$R^{11}$— is —O—$(CH_2)_n$—O— wherein n is 1 or 2;
$R^{12}$ is hydrogen,
  $C_{1-6}$-alkyl, optionally substituted by CN or OH,
  —($C_{1-6}$-alkylene)-$NR^gR^h$,
  —($C_{1-6}$-alkylene)-C(O)—$NR^iR^j$,
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-C(O)$R^f$,
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  —($C_{1-3}$-alkylene)-$R^m$,
    wherein $R^m$ is phenyl, a 5- to 6-membered heteroaryl, 4- to 6-membered heterocycloalkyl or 3 to 6-membered cycloalkyl,
      each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  —$NR^nR^o$;
or $R^{11}$ and $R^{12}$ are bound together to form a ring with the benzo moiety, wherein —$R^{11}$—$R^{12}$— is —O—$(CH_2)_n$—C(O)—,
  —C(O)—$(CH_2)_n$—O—, or
  —O—$(CH_2)_n$—O— wherein n is 1 or 2;
$R^a$, $R^b$, $R^i$ and $R^j$ are each independently
  hydrogen,
  $C_{1-6}$-alkyl,
  —($C_{1-6}$-alkylene)-$NR^kR^l$,
    wherein $R^k$ and $R^l$ are each independently hydrogen or $C_{1-6}$-alkyl,
  or $R^a$ and $R^b$, or $R^i$ and $R^j$ together with the nitrogen to which they are bound form a five or six membered heterocycle comprising one or two heteroatoms selected from the group of nitrogen, oxygen and sulfur;
$R^c$, $R^d$, $R^g$, $R^h$, $R^n$ and $R^o$ are each independently
  hydrogen,
  $C_{1-6}$-alkyl,
  —C(O)$R^e$, or —S(O)$_2R^e$
    wherein $R^e$ is selected from the group of
      hydrogen,
      $C_{1-6}$-alkyl, and
      phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
  or $R^c$ and $R^d$, or $R^n$ and $R^o$ together with the nitrogen to which they are bound form a five or six membered heterocycle comprising one or two heteroatoms selected from the group of nitrogen, oxygen and sulfur;
$R^f$ is selected from the group of
  hydrogen,
  $C_{1-6}$-alkyl,
  $C_{1-6}$-alkoxy; and
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

or a pharmaceutically acceptable salt thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. The present invention provides methods for the treatment of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

In the present description, the term "alkyl," alone or in combination with other groups, refers to a branched or straight-chain monovalent saturated hydrocarbon radical. The term "$C_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene" means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, and the like.

In the present description, the terms "alkoxy" and "$C_{1-6}$-alkoxy" refer to the group R'—O—, wherein R' is alkyl or $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy.

In the present description, the terms "thioalkyl" and "$C_{1-6}$-thioalkyl" refer to the group R'—S—, wherein R' is alkyl or $C_{1-6}$-alkyl as defined above.

The terms "$C_{1-6}$-hydroxyalkyl" and "$C_{1-6}$-alkyl substituted by OH" denote a $C_{1-6}$-alkyl group as defined above wherein at least one of the hydrogen atoms of the alkyl group is replaced by a hydroxyl group.

The terms "$C_{1-6}$-cyanoalkyl" and "$C_{1-6}$-alkyl substituted by CN" denote a $C_{1-6}$-alkyl group as defined above wherein at least one of the hydrogen atoms of the alkyl group is replaced by a CN group.

The terms "halo" and "halogen" refer to fluorine (F), chlorine (Cl), bromine (Br) and iodine (I) with fluorine, chlorine and bromine being preferred.

The term "halo-$C_{1-6}$-alkyl" is synonymous with "$C_{1-6}$-haloalkyl" or "$C_{1-6}$-alkyl substituted by halo" and means a $C_{1-6}$-alkyl group as defined above wherein at least one of the hydrogen atoms of the alkyl group is replaced by a halogen atom, preferably fluoro or chloro, most preferably fluoro. Examples of halo-$C_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-6}$-alkyl groups are difluoro- or trifluoro-methyl or -ethyl.

The term "halo-$C_{1-6}$-alkoxy" is synonymous with "$C_{1-6}$-haloalkoxy" or "$C_{1-6}$-alkoxy substituted by halo" and means a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl," alone or in combination, denotes a straight-chain or branched hydrocarbon residue of 2 to 12 carbon atoms comprising at least one double bond. A preferred sub-group of $C_{2-12}$-alkenyl is $C_{2-6}$-alkyenyl. Examples of the preferred alkenyl groups are ethenyl, propen-1-yl, propen-2-yl(allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "5 or 6 membered heteroaryl" means a monovalent aromatic ring of 5 or 6 ring atoms as ring members containing one, two, or three ring heteroatoms selected from N, O, and S, the rest being carbon atoms. 5 or 6 membered heteroaryl can optionally be substituted with one, two, three or four substituents, wherein each substituent may independently be selected from the group consisting of hydroxy, $C_{1-6}$-alkyl, $C_{1-6}$-alkoxy, $C_{1-6}$-thioalkyl, halo, cyano, nitro, halo-$C_{1-6}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, and carbonylamino, unless otherwise specifically indicated. Preferred substituents are halo, halo-$C_{1-6}$-alkyl, $C_{1-6}$-alkyl, $C_{1-6}$-alkoxy, halo-$C_{1-6}$-alkoxy, nitro, hydroxy or cyano. Examples of heteroaryl moieties include, but are not limited to pyrrolyl, pyrazolyl, imidazolyl, furanyl (synonymous to furyl), thiophenyl (synonymous to thienyl), oxazolyl, isoxazolyl, thiazolyl, isothiazolyl, pyridinyl, pyrimidinyl, pyrazinyl, pyridazinyl, each of which is optionally substituted as described herein.

The term "heterocycloalkyl" means a monovalent saturated ring, consisting of one ring of 3 to 7, preferably from 4 to 6 atoms as ring members, including one, two, or three heteroatoms selected from nitrogen, oxygen and sulfur, the rest being carbon atoms. 3 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, cyano, nitro, halo-$C_{1-6}$-alkyl, $C_{1-6}$-hydroxyalkyl, $C_{1-6}$-alkoxycarbonyl, amino, $C_{1-6}$-alkylamino, di($C_{1-6}$)alkylamino, aminocarbonyl, or carbonylamino, unless otherwise specifically indicated. Preferred substituents are halo, halo-$C_{1-6}$-alkyl, $C_{1-6}$-alkyl, $C_{1-6}$-alkoxy, halo-$C_{1-6}$-alkoxy, nitro, hydroxy or cyano. Examples of heterocyclic moieties include, but are not limited to, oxiranyl, thiiranyl, oxetanyl, tetrahydro-furanyl, tetrahydro-thiophenyl (synonymous to tetrahydro-thienyl), pyrrolidinyl, pyrazolidinyl, imidazolidinyl, oxazidinyl, isoxazidinyl, thiazolidinyl, isothiazolidinyl, piperidinyl, piperazidinyl, morpholinyl, or tetrahydropyranyl, each of which is optionally substituted as described herein.

The term "heterocycle" in the definition "$R^a$ and $R^b$, $R^c$ and $R^d$, $R^i$ and $R^j$, or $R^n$ and $R^o$, together with the nitrogen to which they are bound form a five- or six-membered heterocycle comprising one or two heteroatoms selected from the group of nitrogen, oxygen and sulfur" means either heterocycloalkyl or heteroaryl in the above-given sense which may optionally be substituted as described above. Preferably, the "heterocycle" may optionally be substituted with one, two or three substituents selected from halo, halo-$C_{1-6}$-alkyl, $C_{1-6}$-alkyl, $C_{1-6}$-alkoxy, halo-$C_{1-6}$-alkoxy, nitro, and cyano. Preferred heterocycles are optionally substituted piperazine, N-methylpiperazine, morpholin, piperidine and pyrrolidine.

The term "$C_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, $C_{1-6}$-alkyl, $C_{1-6}$-alkoxy, halogen, amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "one or more" substituents preferably means one, two or three substituents per ring.

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The invention further comprises individual optical isomers of the compounds herein as well as racemic and non-racemic mixtures thereof.

In detail, the present invention provides compounds of formula (I)

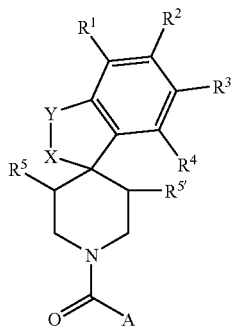

(I)

wherein
X is O and Y is $CH_2$, or
X is O and Y is C=O, or
X is C=O and Y is $NR^6$, or
X—Y is CH=CH, or
X—Y is $CH_2$—$CH_2$, or
X is C=O and Y is O, or
X is $CH_2$ and Y is $NR^6$, or
X is $CH_2$ and Y is O;

A is selected from the group consisting of

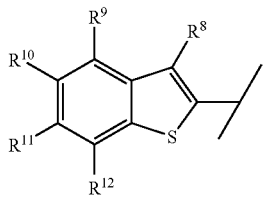

(a)

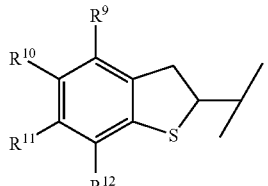

(b)

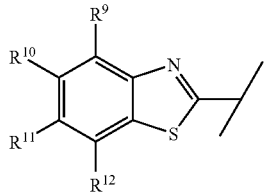

(c)

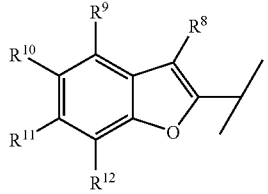

(d)

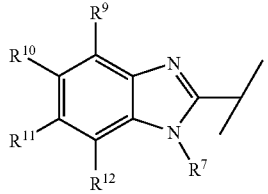

(e)

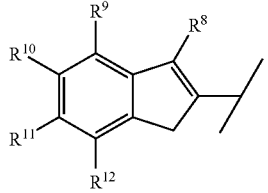

(f)

and

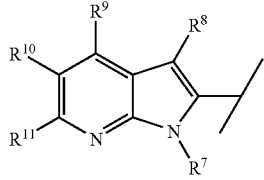

(g)

$R^1$, $R^2$, $R^3$ and $R^4$ are each independently
hydrogen,
halo,
$C_{1-6}$-alkyl, optionally substituted by OH
halo-$C_{1-6}$-alkyl,
$C_{1-6}$-alkoxy, optionally substituted by OH, or
halo-$C_{1-6}$-alkoxy;
$R^5$ and $R^{5'}$ are each independently hydrogen or methyl;
$R^6$ is hydrogen or $C_{1-6}$-alkyl;
$R^7$ is hydrogen,
$C_{1-6}$-alkyl, optionally substituted by CN or OH, or
—($C_{1-6}$-alkylene)-C(O)—$NR^aR^b$;
$R^8$ is hydrogen,
$C_{1-6}$-alkyl,
$C_{1-6}$-alkoxy, —(C$_{1-6}$-alkylene)-NR$^c$R$^d$,
—(C$_{1-6}$-alkylene)-C(O)R$^f$,
benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
R$^9$ is hydrogen, halo, C$_{1-6}$-alkyl, or C$_{1-6}$-alkoxy;
R$^{10}$ is hydrogen, halo, C$_{1-6}$-alkyl, halo-C$_{1-6}$-alkyl, C$_{1-6}$-alkoxy, halo-C$_{1-6}$-alkoxy, or —O—C$_{2-10}$-alkenyl;
R$^{11}$ is hydrogen, halo, C$_{1-6}$-alkyl, or C$_{1-6}$-alkoxy;
or R$^{10}$ and R$^{11}$ are bound together to form a ring with the benzo moiety, wherein —R$^{10}$—R$^{11}$— is —O—(CH$_2$)$_n$—O— wherein n is 1 or 2;
R$^{12}$ is hydrogen,
C$_{1-6}$-alkyl, optionally substituted by CN or OH,
—(C$_{1-6}$-alkylene)-NR$^g$R$^h$,
—(C$_{1-6}$-alkylene)-C(O)—NR$^i$R$^j$,
—O-benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
nitro,
halo,
cyano,
C$_{1-6}$-alkoxy,
halo-C$_{1-6}$-alkoxy,
halo-C$_{1-6}$-alkyl,
—(C$_{1-6}$-alkylene)-C(O)R$^f$,
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
—(C$_{1-3}$-alkylene)-R$^m$,
wherein R$^m$ is phenyl, a 5- to 6-membered heteroaryl, 4- to 6-membered heterocycloalkyl or 3 to 6-membered cycloalkyl,
each optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
—NR$^n$R$^o$;
or R$^{11}$ and R$^{12}$ are bound together to form a ring with the benzo moiety, wherein —R$^{11}$—R$^{12}$— is —O—(CH$_2$)$_n$—C(O)—,
—C(O)—(CH$_2$)$_n$—O—, or
—O—(CH$_2$)$_n$—O— wherein n is 1 or 2;
R$^a$, R$^b$, R$^i$ and R$^j$ are each independently
hydrogen,
C$_{1-6}$-alkyl,
—(C$_{1-6}$-alkylene)-NR$^k$R$^l$,
wherein R$^k$ and R$^l$ are each independently hydrogen or C$_{1-6}$-alkyl,
or R$^a$ and R$^b$, or R$^i$ and R$^j$ together with the nitrogen to which they are bound form a five or six membered heterocycle comprising one or two heteroatoms selected from the group of nitrogen, oxygen and sulfur;
R$^c$, R$^d$, R$^g$, R$^h$, R$^n$ and R$^o$ are each independently
hydrogen,
C$_{1-6}$-alkyl,
—C(O)R$^e$, or —S(O)$_2$R$^e$
wherein R$^e$ is selected from the group of
hydrogen,
C$_{1-6}$-alkyl, and
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
or R$^c$ and R$^d$, or R$^n$ and R$^o$ together with the nitrogen to which they are bound form a five or six membered heterocycle comprising one or two heteroatoms selected from the group of nitrogen, oxygen and sulfur;
R$^f$ is selected from
hydrogen,
C$_{1-6}$-alkyl,
C$_{1-6}$-alkoxy; and
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;

or a pharmaceutically acceptable salt thereof.

In certain embodiments of the invention, R$^a$ and R$^b$, R$^c$ and R$^d$, R$^i$ and R$^j$, or R$^n$ and R$^o$ together with the nitrogen to which they are bound may form piperazine, 4-(C$_{1-6}$-alkyl)-piperazine, 4-methylpiperazine, morpholine, piperidine or pyrrolidine.

In certain embodiments of the invention, R$^a$ and R$^b$, R$^c$ and R$^d$, R$^i$ and R$^j$, or R$^n$ and R$^o$ together with the nitrogen to which they are bound may form 4-methylpiperazine, or morpholine, in particular morpholine.

In certain embodiments of the invention, wherein R$^m$ is a 5- to 6-membered heteroaryl, the preferred heteroaryl is selected from the group consisting of pyridine, pyrimidine, pyrazine, pyridazine, imidazole, pyrazole, oxazole, and isoxazole. All these residues are optionally substituted as described herein.

In embodiments of the invention, wherein R$^m$ is a 4- to 6-membered heterocycloalkyl, the preferred heterocycloalkyl is selected from the group consisting of pyrrolidine, oxethane, tetrahydropyrane, piperidine, morpholine, and piperazine. All these residues are optionally substituted as described herein.

In certain embodiments of the invention,
R$^1$, R$^2$, R$^3$ and R$^4$ are each independently
hydrogen,
halo, or
C$_{1-6}$-alkoxy, optionally substituted by OH.

In certain embodiments of the invention, R$^1$ is hydrogen; R$^2$ is hydrogen or C$_{1-6}$-alkoxy, R$^3$ is hydrogen, halo, or C$_{1-6}$-alkoxy, optionally substituted by OH; and R$^4$ is hydrogen.

In certain embodiments all R$^1$ to R$^4$ are hydrogen.

In certain embodiments, one residue of R$^1$ to R$^4$ is halo and the others are hydrogen.

In certain embodiments, one residue of R$^1$ to R$^4$ is C$_{1-6}$-alkoxy, optionally substituted by OH, preferably methoxy or —O(CH$_2$)$_2$OH, and the others are hydrogen.

In certain embodiments of the invention, R$^5$ and R$^{5'}$ are both hydrogen, in other embodiments of the invention, R$^5$ and R$^{5'}$ are both methyl, in other embodiments of the invention, R$^5$ is hydrogen and R$^{5'}$ is methyl.

In certain embodiments of the invention, R$^5$ is hydrogen, R$^{5'}$ is methyl, X is O and Y is C═O.

In certain embodiments of the invention, R$^6$ is hydrogen or C$_{1-6}$-alkyl, preferably hydrogen.

In certain embodiments of the invention,
R$^7$ is hydrogen,
C$_{1-6}$-alkyl, optionally substituted by CN or OH, or
—(C$_{1-6}$-alkylene)-C(O)—NR$^a$R$^b$,
wherein R$^a$ and R$^b$ are each independently hydrogen or C$_{1-6}$-alkyl.
Preferably, R$^7$ is hydrogen.
In certain embodiments of the invention,
R$^8$ is hydrogen,
C$_{1-6}$-alkyl, or
C$_{1-6}$-alkoxy,
—(C$_{1-6}$-alkylene)-NR$^c$R$^d$,
wherein R$^c$ and R$^d$ are each independently hydrogen,
—C(O)R$^e$, or —S(O)$_2$R$^e$
   wherein R$^e$ is selected from the group of
      hydrogen,
      C$_{1-6}$-alkyl, and
      phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
—(C$_{1-6}$-alkylene)-C(O)R$^f$,
   wherein R$^f$ is
      hydrogen,
      C$_{1-6}$-alkyl,
      C$_{1-6}$-alkoxy, or
      phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano.

Preferably, R$^8$ is hydrogen; C$_{1-6}$-alkyl, preferably methyl; or C$_{1-6}$-alkoxy, preferably methoxy or —O-iso-propyl.

In a certain embodiment of the invention, R$^9$ is hydrogen, halo or C$_{1-6}$-alkoxy. Preferably, R$^9$ is hydrogen or C$_{1-6}$-alkoxy.

In certain embodiments of the invention, R$^9$ is hydrogen; halo, preferably fluoro, chloro or bromo; C$_{1-6}$-alkyl, preferably methyl; C$_{1-6}$-alkoxy, preferably methoxy or —O-iso-propyl; halo-C$_{1-6}$-alkoxy, preferably trifluoromethoxy; or —O—C$_{2-10}$-alkenyl, preferably allyl.

In certain embodiments of the invention, R$^{10}$ is hydrogen; halo, preferably bromo or chloro; C$_{1-6}$-alkyl, preferably methyl; or C$_{1-6}$-alkoxy, preferably methoxy.

In certain embodiments of the invention, R$^{11}$ is hydrogen; halo, preferably bromo or chloro; C$_{1-6}$-alkyl, preferably methyl; or C$_{1-6}$-alkoxy, preferably methoxy. More preferably, R$^{11}$ is hydrogen.

In certain embodiments of the invention
R$^{12}$ is hydrogen,
   C$_{1-6}$-alkyl, optionally substituted by CN or OH,
   —(C$_{1-6}$-alkylene)-NR$^g$R$^h$, wherein R$^g$ and R$^h$ are each independently
      hydrogen,
      C$_{1-6}$-alkyl,
      —C(O)R$^e$, or —S(O)$_2$R$^e$, wherein R$^e$ is selected from
         hydrogen,
         C$_{1-6}$-alkyl, and
         phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
   —(C$_{1-16}$-alkylene)-C(O)—NR$^i$R$^j$, wherein R$^i$ and R$^j$ are each independently
      hydrogen,
      C$_{1-6}$-alkyl,
      —(C$_{1-6}$-alkylene)-NR$^k$R$^l$,
         wherein R$^k$ and R$^l$ are each independently hydrogen or C$_{1-6}$-alkyl,
      or R$^i$ and R$^j$ together with the nitrogen to which they are bound form a five or six membered heterocycle comprising one or two heteroatoms selected from the group of nitrogen, oxygen and sulfur;
   —O-benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
   nitro,
   halo,
   cyano,
   C$_{1-6}$-alkoxy,
   halo-C$_{1-6}$-alkoxy,
   halo-C$_{1-6}$-alkyl,
   —(C$_{1-6}$-alkylene)-C(O)R$^f$, wherein R$^f$ is
      C$_{1-6}$-alkyl,
      C$_{1-6}$-alkoxy, or
      phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
   phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano,
   —(C$_{1-3}$-alkylene)-R$^m$,
      wherein R$^m$ is phenyl, a 5- to 6-membered heteroaryl, 4- to 6-membered heterocycloalkyl or 3 to 6-membered cycloalkyl,
      each optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
   —NR$^n$R$^o$,
      wherein R$^n$ and R$^o$ are each independently
         hydrogen,
         C$_{1-6}$-alkyl,
         or R$^n$ and R$^o$ together with the nitrogen to which they are bound form a five or six membered heterocycle comprising one or two heteroatoms selected from the group of nitrogen, oxygen and sulfur.

In certain embodiments of the invention,
R$^{12}$ is hydrogen,
   C$_{1-6}$-alkyl, optionally substituted by CN or OH,
   C$_{1-6}$-alkoxy, or
   —NR$^n$R$^o$,
      wherein R$^n$ and R$^o$ are each independently
         hydrogen,
         C$_{1-6}$-alkyl,
         or R$^n$ and R$^o$ together with the nitrogen to which they are bound form a five or six membered heterocycle comprising one or two heteroatoms selected from the group of nitrogen, oxygen.

In certain embodiments of the invention, namely in combination with any embodiment described herein, R$^7$, R$^8$, R$^9$, R$^{10}$, R$^{11}$ and R$^{12}$ are not simultaneously hydrogen.

In certain embodiments of the invention, X is O and Y is CH$_2$, A is selected from the group consisting of (a), (b), (c), (d) and (e); and R$^1$ to R$^5$ and R$^7$ to R$^{12}$ are as defined above.

In certain embodiments of the invention, X is O and Y is C=O, A is (f) or (g), and R$^1$ to R$^5$ and R$^7$ to R$^{12}$ are as defined above.

In certain embodiments of the invention, X is C=O and Y is NR$^6$, A is (f), and R$^1$ to R$^{12}$ are as defined above.

In certain embodiments of the invention, X—Y is CH=CH, and A is (f) or (g), and R$^1$ to R$^5$ and R$^7$ to R$^{12}$ are as defined above.

In one embodiment
X is O and Y is CH$_2$,
X is O and Y is C=O,
X is C=O and Y is O, or
X is CH$_2$ and Y is O.
In another embodiment
X is C=O and Y is NR$^6$, or
X is CH$_2$ and Y is NR$^6$.
In yet another embodiment
X—Y is CH=CH, or
X—Y is CH$_2$—CH$_2$.

Preferred X and Y are:

X is O and Y is $CH_2$,

X is O and Y is C=O,

X is C=O and Y is $NR^6$,

X—Y is CH=CH, or

X—Y is $CH_2$—$CH_2$.

Preferred compounds of the invention are:

1'-(1-Benzothien-2-ylcarbonyl)-3H-spiro[2-benzofuran-1,4'-piperidine],

1'-[(7-Methoxy-1-benzothien-2-yl)carbonyl]-3H-spiro[2-benzofuran-1,4'-piperidine], 1'-[(3-Isopropoxy-1-benzothien-2-yl)carbonyl]-3H-spiro[2-benzofuran-1,4'-piperidine], 1'-[(5-Methoxy-2,3-dihydro-1-benzothien-2-yl)carbonyl]-3H-spiro[2-benzofuran-1,4'-piperidine], 1'-[(4-Methoxy-7-morpholin-4-yl-1,3-benzothiazol-2-yl)carbonyl]-3H-spiro[2-benzofuran-1,4'-piperidine], 1'-[(5-Bromo-7-ethyl-1-benzofuran-2-yl)carbonyl]-3H-spiro[2-benzofuran-1,4'-piperidine], 1'-(1-Benzimidazol-2-ylcarbonyl)-3H-spiro[2-benzofuran-1,4'-piperidine], 1'-[(5-Methyl-1H-benzimidazol-2-yl)carbonyl]-3H-spiro[2-benzofuran-1,4'-piperidine], 1'-[(5-Chloro-1H-benzimidazol-2-yl)carbonyl]-3H-spiro[2-benzofuran-1,4'-piperidine], (1RS,3'SR)-3'-Methyl-1'-[(3-methyl-1H-inden-2-yl)carbonyl]-3H-spiro[2-benzofuran-1,4'-piperidin]-3-one, 6-Methoxy-1'-[(3-methyl-3H-inden-2-yl)carbonyl]-3H-spiro[2-benzofuran-1,4'-piperidin]-3-one, 5-Methoxy-1'-[(3-methyl-1H-inden-2-yl)carbonyl]-3H-spiro[2-benzofuran-1,4'-piperidin]-3-one, 1'-(1H-Pyrrolo[2,3-b]pyridin-2-ylcarbonyl)-3H-spiro[2-benzofuran-1,4'-piperidin]-3-one, 6-Methoxy-1'-(1H-pyrrolo[2,3-b]pyridin-2-ylcarbonyl)-3H-spiro[2-benzofuran-1,4'-piperidin]-3-one, 6-(2-Hydroxyethoxy)-1'-(1H-pyrrolo[2,3-b]pyridin-2-ylcarbonyl)-3H-spiro[2-benzofuran-1,4'-piperidin]-3-one, 5-Bromo-1'-[(3-methyl-1H-inden-2-yl)carbonyl]spiro[indole-3,4'-piperidin]-2(1H)-one, 1'-[(3-Methyl-1H-inden-2-yl)carbonyl]spiro[indene-1,4'-piperidine], and 1'-(1H-Pyrrolo[2,3-b]pyridin-2-ylcarbonyl)spiro[indene-1,4'-piperidine].

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprises administering a therapeutically effective amount of a compound of formula (I), (Ia), (Ib), (Ic), (Id), (Ie), (If), or (Ig).

The invention also encompasses a pharmaceutical composition comprising a compound of formula (I), (Ia), (Ib), (Ic), (Id), (Ie), (If), or (Ig) and a pharmaceutically acceptable carrier. The pharmaceutical composition may further comprise at least one pharmaceutically acceptable excipient.

In a certain embodiment, the compound of the invention of general formula (I) can be manufactured according to a process comprising reacting a compound of formula (II):

with a carboxylic acid of the formula III wherein $R^1$ to $R^{5'}$, X, Y and A are as defined above.

The synthesis of compounds of general formula (I) will be described in more detail below and in the examples.

General Scheme A

Compounds of formula (I) can be prepared via an amide coupling between a spiropiperidine derivative of formula (II) and a carboxylic acid $A$-$CO_2H$ (III), wherein A is defined as hereinabove. The usual reagents and protocols known in the art can be used to effect the amide coupling. Spiropiperine derivatives of formula (II) and carboxylic acids (III) are either commercially available or readily prepared using procedures described hereinafter or using methods known in the art starting from commercially available materials. General scheme A is hereinafter further illustrated with general procedure I.

General Procedure I: Amide Coupling:

To a 0.1 M stirred solution of a carboxylic acid derivative in $CH_2Cl_2$ are added EDC (1.3 eq), HOBt (1.3 eq), $Et_3N$ (1.3 eq) and the spiropiperidine derivative (1 eq). The mixture is stirred over night at RT and then poured onto water and extracted with $CH_2Cl_2$. The combined organic phases are dried over $Na_2SO_4$ and concentrated in vacuo. Flash chromatography or preparative HPLC affords the title compound.

The compounds of the present invention exhibit V1a activity, which may be detected as described below:

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)); homogenized with Polytron for 1 min; and sonicated on ice for 2×2 minutes at 80% intensity (Vibracell sonicator). The preparation was centrifuged 20 min at 500 g at 4° C., the pellet was discarded and the supernatant centrifuged 1 hour at 43,000 g at 4° C. (19,000 rpm). The pellet was resuspended in 12.5 ml Lysis buffer+ 12.5 ml Sucrose 20% and homogenized using a Polytron for 1-2 min. The protein concentration was determined by the Bradford method and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts were subtracted from each well and data was normalized to the maximum specific binding set at 100%. To calculate an IC 50 the curve was fitted using a non-linear regression model (XLfit), and the Ki was calculated using the Cheng-Prussoff equation.

| Example | pKi hV1a |
|---|---|
| 1 | 7.6 |
| 2 | 7.3 |
| 4 | 7.2 |
| 6 | 7.3 |
| 9 | 7.5 |
| 10 | 7.2 |
| 14 | 6.7 |

The present invention also provides pharmaceutical compositions containing compounds of the invention, for example compounds of formula (Ia), (Ib), (Ic), (Id), (Ie), (If), and (g), and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which the compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

EXAMPLE C

Suppositories of the following composition can be manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture then can be poured into suppository moulds of suitable size, left to cool; the suppositories can then be removed from the moulds and packed individually in wax paper or metal foil.

In the following, the synthesis of compounds of formula (I) is further exemplified: The compounds of formula I may be prepared in accordance with the process variants as described above. The starting materials described in the Example section are either commercially available or are otherwise known or derived from the chemical literature, for instance as cited below, or may be prepared as described in the Examples section.

EXAMPLES

Example 1

1'-(1-Benzothien-2-ylcarbonyl)-3H-spiro[2-benzofuran-1,4'-piperidine]

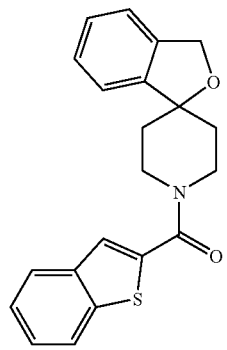

Amide coupling according to general procedure I:
Amine: 3H-Spiro[2-benzofuran-1,4'-piperidine] (described in *J. Org. Chem.* 1976, 41, 2628),
Acid: Benzo[b]thiophene-2-carboxylic acid,
ES-MS m/e (%): 350.2 (M+H$^+$).

Example 2

1'-[(7-Methoxy-1-benzothien-2-yl)carbonyl]-3H-spiro[2-benzofuran-1,4'-piperidine]

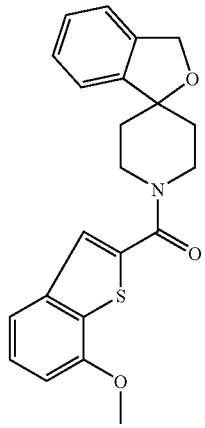

Amide coupling according to general procedure I:
Amine: 3H-Spiro[2-benzofuran-1,4'-piperidine] (described in *J. Org. Chem.* 1976, 41, 2628),
Acid: 7-Methoxy-benzo[b]thiophene-2-carboxylic acid,
ES-MS m/e (%): 380.1 (M+H$^+$).

Example 3

1'-[(3-Isopropoxy-1-benzothien-2-yl)carbonyl]-3H-spiro[2-benzofuran-1,4'-piperidine]

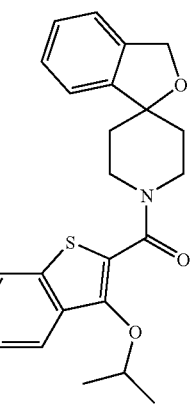

Amide coupling according to general procedure I:
Amine: 3H-Spiro[2-benzofuran-1,4'-piperidine] (described in *J. Org. Chem.* 1976, 41, 2628),
Acid: 3-Isopropoxy-benzo[b]thiophene-2-carboxylic acid (described in *J. Med. Chem.* 1992, 35, 958),
ES-MS m/e (%): 408.2 (M+H$^+$).

Example 4

1'-[(5-Methoxy-2,3-dihydro-1-benzothien-2-yl)carbonyl]-3H-spiro[2-benzofuran-1,4'-piperidine]

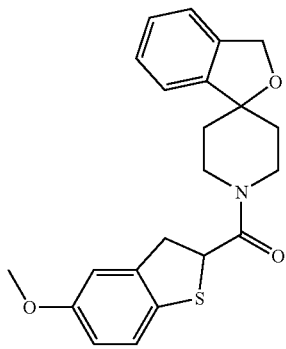

Amide coupling according to general procedure I:
Amine: 3H-Spiro[2-benzofuran-1,4'-piperidine] (described in *J. Org. Chem.* 1976, 41, 2628),
Acid: 5-Methoxy-2,3-dihydro-benzo[b]thiophene-2-carboxylic acid
ES-MS m/e (%): 381.0 (M+H$^+$).

5-Methoxy-2,3-dihydro-benzo[b]thiophene-2-carboxylic acid

From the commercially available 5-methoxy-benzo[b]thiophene-2-carboxylic acid was prepared 5-methoxy-2,3-dihydro-benzo[b]thiophene-2-carboxylic acid by reduction using known procedures. One example is Mg/MeOH.

Example 5

1'-[(4-Methoxy-7-morpholin-4-yl-1,3-benzothiazol-2-yl)carbonyl]-3H-spiro[2-benzofuran-1,4'-piperidine]

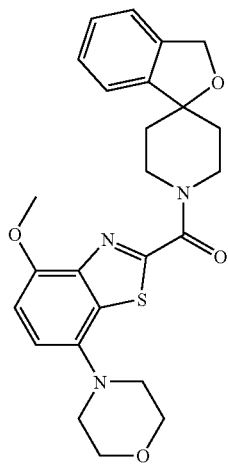

Amide coupling according to general procedure I:
Amine: 3H-Spiro[2-benzofuran-1,4'-piperidine] (described in *J. Org. Chem.* 1976, 41, 2628),
Acid: 4-Methoxy-7-morpholin-4-yl-benzothiazole-2-carboxylic acid (described in patent WO2003045385)
ES-MS m/e (%): 466.6 (M+H$^+$).

Example 6

1'-[(5-Bromo-7-ethyl-1-benzofuran-2-yl)carbonyl]-3H-spiro[2-benzofuran-1,4'-piperidine]

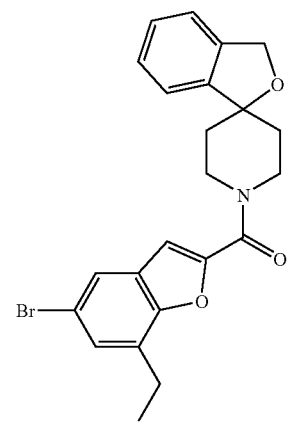

Amide coupling according to general procedure I:
Amine: 3H-Spiro[2-benzofuran-1,4'-piperidine] (described in *J. Org. Chem.* 1976, 41, 2628),
Acid: 5-Bromo-7-ethyl-benzofuran-2-carboxylic acid
ES-MS m/e (%): 442.0 (M+H$^+$).

Example 7

1'-(1H-Benzimidazol-2-ylcarbonyl)-3H-spiro[2-benzofuran-1,4'-piperidine]

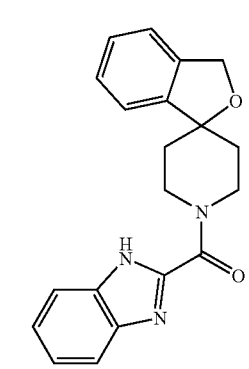

Amide coupling according to general procedure I:
Amine: 3H-Spiro[2-benzofuran-1,4'-piperidine] (described in *J. Org. Chem.* 1976, 41, 2628),
Acid: 1H-Benzoimidazole-2-carboxylic acid,
ES-MS m/e (%): 334.2 (M+H$^+$).

Example 8

1'-[(5-Methyl-1H-benzimidazol-2-yl)carbonyl]-3H-spiro[2-benzofuran-1,4'-piperidine]

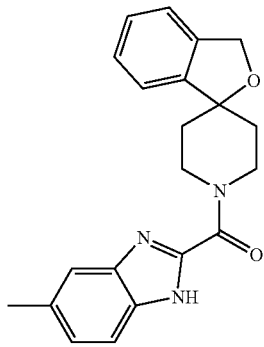

Amide coupling according to general procedure I:
Amine: 3H-Spiro[2-benzofuran-1,4'-piperidine] (described in *J. Org. Chem.* 1976, 41, 2628),
Acid: 5-Methyl-1H-benzoimidazole-2-carboxylic acid,
ES-MS m/e (%): 348.1 (M+H$^+$).

Example 9

1'-[(5-Chloro-1H-benzimidazol-2-yl)carbonyl]-3H-spiro[2-benzofuran-1,4'-piperidine]

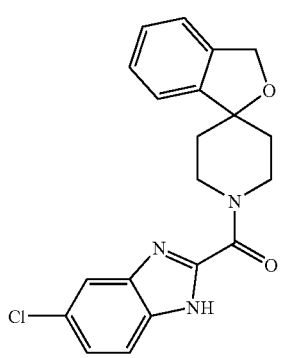

Amide coupling according to general procedure I:
Amine: 3H-Spiro[2-benzofuran-1,4'-piperidine] (described in *J. Org. Chem.* 1976, 41, 2628),
Acid: 5-Chloro-1H-benzoimidazole-2-carboxylic acid,
ES-MS m/e (%): 368.0 (M+H$^+$).

Example 10

(1RS,3'SR)-3'-Methyl-1'-[(3-methyl-1H-inden-2-yl)carbonyl]-3H-spiro[2-benzofuran-1,4'-piperidin]-3-one

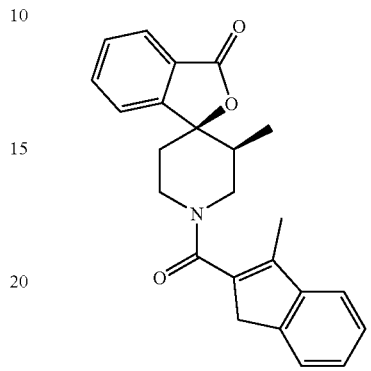

Amide coupling according to general procedure I:
Amine: (1RS,3'SR)-3'-Methyl-3H-spiro[2-benzofuran-1,4'-piperidin]-3-one (prepared according to WO 9929696)
Acid: 3-Methyl-1H-indene-2-carboxylic acid,
ES-MS m/e (%): 374.5 (M+H$^+$).

Example 11

6-Methoxy-1'-[(3-methyl-1H-inden-2-yl)carbonyl]-3H-spiro[2-benzofuran-1,4'-piperidin]-3-one

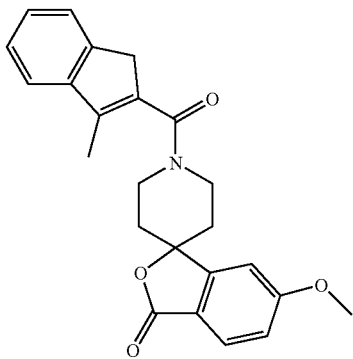

Amide coupling according to general procedure I:
Amine: 6-Methoxy-3H-spiro[2-benzofuran-1,4'-piperidin]-3-one (prepared according to EP 722941)
Acid: 3-Methyl-1H-indene-2-carboxylic acid,
ES-MS m/e (%): 390.5 (M+H$^+$).

Example 12

5-Methoxy-1'-[(3-methyl-1H-inden-2-yl)carbonyl]-3H-spiro[2-benzofuran-1,4'-piperidin]-3-one

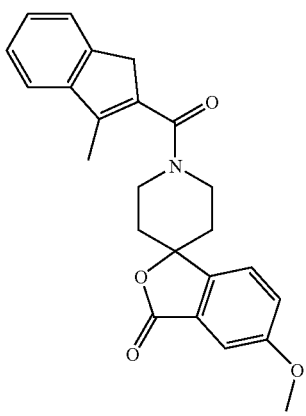

Amide coupling according to general procedure I:
Amine: 5-Methoxy-3H-spiro[2-benzofuran-1,4'-piperidin]-3-one (described in EP 722941)
Acid: 3-Methyl-1H-indene-2-carboxylic acid,
ES-MS m/e (%): 390.5 (M+H$^+$).

Example 13

1'-(1H-Pyrrolo[2,3-b]pyridin-2-ylcarbonyl)-3H-spiro[2-benzofuran-1,4'-piperidin]-3-one

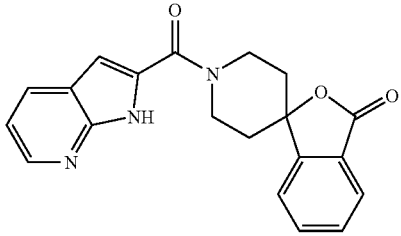

Amide coupling according to general procedure I:
Amine: 3H-Spiro[2-benzofuran-1,4'-piperidin]-3-one (preparation described in Organic Process Research & Development (2006), 10(4), 822-828.)
Acid: 1H-Pyrrolo[2,3-b]pyridine-2-carboxylic acid,
ES-MS m/e (%): 348.4 (M+H$^+$).

Example 14

6-Methoxy-1'-(1H-pyrrolo[2,3-b]pyridin-2-ylcarbonyl)-3H-spiro[2-benzofuran-1,4'-piperidin]-3-one

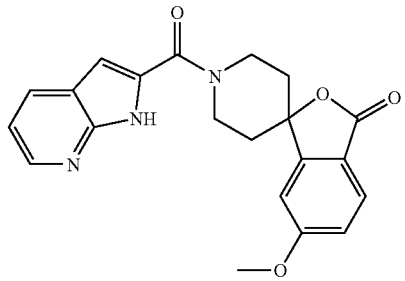

Amide coupling according to general procedure I:
Amine: 6-Methoxy-3H-spiro[2-benzofuran-1,4'-piperidin]-3-one (preparation described in EP 722941)
Acid: 1H-Pyrrolo[2,3-b]pyridine-2-carboxylic acid,
ES-MS m/e (%): 378.4 (M+H$^+$).

Example 15

6-(2-Hydroxyethoxy)-1'-(1H-pyrrolo[2,3-b]pyridin-2-ylcarbonyl)-3H-spiro[2-benzofuran-1,4'-piperidin]-3-one

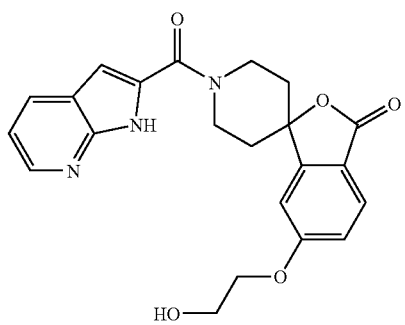

Amide coupling according to general procedure I:
Amine: 6-(2-Hydroxyethoxy)-3H-spiro[2-benzofuran-1,4'-piperidin]-3-one (preparation described in EP 722941)
Acid: 1H-Pyrrolo[2,3-b]pyridine-2-carboxylic acid,
ES-MS m/e (%): 408.4 (M+H$^+$).

6-(2-Hydroxyethoxy)-1'-3H-spiro[2-benzofuran-1,4'-piperidin]-3-one

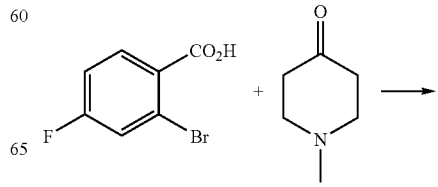

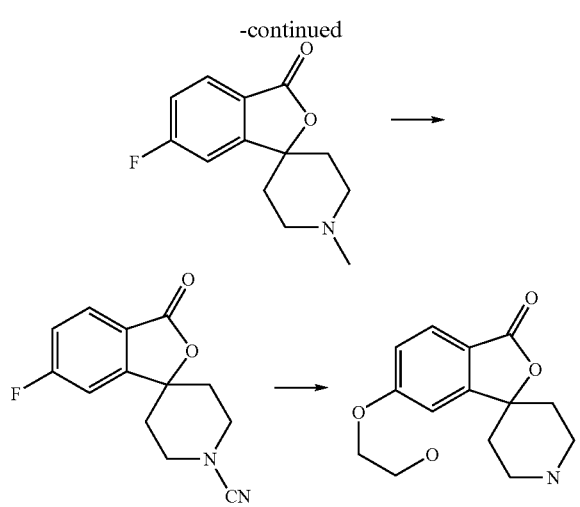

Preparation of N-Methylated Lactone Intermediate

To a solution of the substituted ortho-bromo benzoic acid (10.9 g, 50 mmol) in dry THF (200 ml) at −78° C. n-butyllithium (1.6 M in hexanes) (100 mmol) was added drop wise (3 h) and the resulting solution was stirred for an additional 2 h at the same temperature. Freshly distilled N-methyl 4-piperidone (7.91 g, 70 mmol) in dry hexane (25 ml) was added over 30 min at the same temperature. The mixture was then allowed to stir at rt and was finally added to ether (200 ml) and water (300 ml). The basic (aqueous) layer was extracted with ether (5×100 ml) and the aqueous layer was acidified with concentrated hydrochloric acid (pH 2-3) and extracted with ether. The aqueous solution was boiled for 1 h and was then cooled to 0-5° C. and made alkaline (pH 9-10) with cold aqueous sodium hydroxide. The cold solution was rapidly extracted with chloroform (5×200 ml). The combined chloroform extracts were washed with water, dried, concentrated to give light yellow solid which was purified over neutral alumina eluting with a gradient of 30-50% ethyl acetate-hexane to obtain 1.75 g (15%) of N-methylated lactone as white solid. 1H-NMR (CDCl3, 400 MHz): δ1.68-1.75 (m, 2H), 2.18-2.19 (m, 1H), 2.38 (s, 3H), 2.44-2.52 (m, 2H), 2.68-2.84 (m, 2H), 2.84-2.85 (m, 1H), 7.02-7.05 (m, 1H), 7.19-7.22 (m, 1H), 7.84-7.87 (m, 1H); FIA-MS: 236 (M+1).

Preparation of Cyano-Piperidine Intermediate

To a solution of the N-methylated lactone from above (1.17 g, 5 mmol) in dry chloroform (10 ml) was added cyanogenbromide (60 nmol) and the resulting solution was refluxed for 36 h. The reaction mixture was extracted with 5% HCl (5 ml) and then with water (2.5 ml). The chloroform solution was dried (anhydrous MgSO4) and concentrated to give a pale yellow solid which was chromatographed over SiO2 eluting with 1% MeOH—CH2Cl2 to give 858 mg (70%) of the desired Cyano-piperidine as white solid. 1H-NMR (CDCl3, 400 MHz): δ1.72-1.76 (m, 2H), 2.22-2.30 (m, 1H), 3.48-3.60 (m, 4H), 7.09-7.11 (m, 1H), 7.11-7.28 (m, 1H), 7.89-7.92 (m, 1H); IR (KBr): 3492, 3043, 2216, 1760, 1602, 1478 cm−1.

Preparation of 6-(2-hydroxyethoxy)-3H-spiro[2-benzofuran-1,4'-piperidin]-3-one

The above cyano-piperidine (1.23 g, 5 mmol) was heated with ethylene glycol (5 ml) and sodium hydroxide (0.82 g, 20.5 mmol) for 15-20 min at 130° C. Most of the ethylene glycol was removed by distillation under high vacuum. The residual reaction mixture was diluted with water and extracted repeatedly with chloroform. The combined organics was dried and concentrated to give a semi solid material which was purified over Al2O3 column upon elution with 5-7% MeOH2Cl2 containing NH3 (aqueous) to yield 789 mg (60%) of 6-(2-hydroxyethoxy)-3H-spiro[2-benzofuran-1,4'-piperidin]-3-one as pale yellow solid. 1H-NMR (d6-DMSO, 400 MHz): δ1.47-1.50 (m, 2H), 2.03-2.10 (m, 2H0, 2.79-2.85 (m, 2H), 2.95-2.97 (m, 2H), 3.73-3.76 (m, 2H), 4.12-4.14 (m, 2H), 7.09 (d, J=8.4 Hz, 1H), 7.20 (s, 1H), 7.69 (d, J=8.4 Hz, 1H); 13C-NMR (d6-DMSO, 100 MHz): ☐☐35.9, 42.3, 59.3, 70.4, 84.6, 106.4, 116.6, 117.0, 126.8, 156.9, 163.9, 168.5; FIA-MS: 264.3 (M+1).

Example 16

5-Bromo-1'-[(3-methyl-1H-inden-2-yl)carbonyl] spiro[indole-3,4'-piperidin]-2(1H)-one

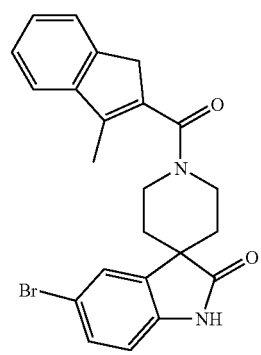

Amide coupling according to general procedure I:
Amine: 5-Bromo-spiro[indole-3,4'-piperidin]-2(1H)-one (prepared described herein below)
Acid: 3-Methyl-1H-indene-2-carboxylic acid,
ES-MS m/e (%): 437.4 (M+H+).

5-bromo-spiro[indole-3,4'-piperidin]-2(1H)-one

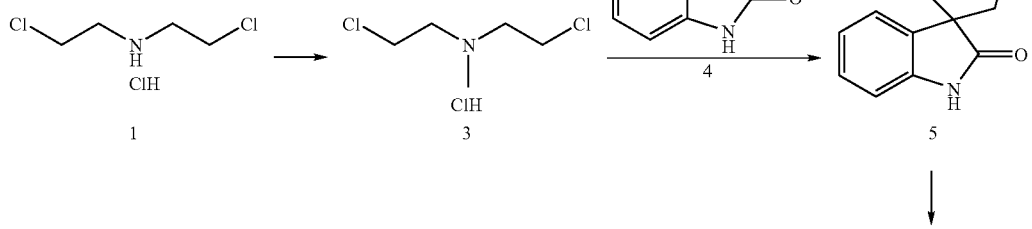

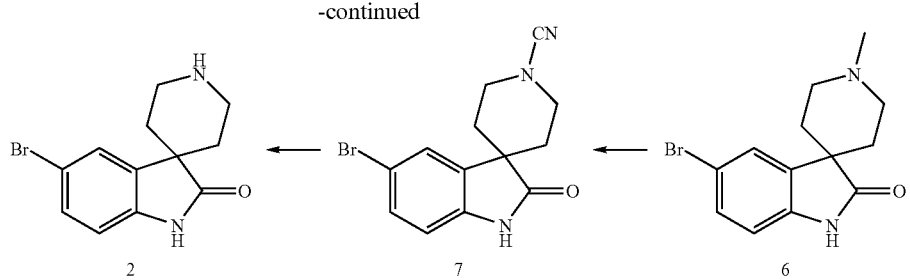

1,5-Dichloro-3-methyl-3-azapentane hydrochloride 3

Formic acid (10.0 g; 0.2 mol) and 37% formaldehyde (20 ml) were mixed in a 250 ml round-bottom flask equipped with reflux condenser. 1,5-Dichloro-3-azapentane, hydrochloride (17.0 g; 0.1 mol) was added and the solution was heated with magnetic stirring at 100 C. After 3 h the temperature was increased to 120 C for 20 min and finally allowed to cool to room temperature before the solvent was evaporated in vacuo to afford 3 as white solid in quantitative yield. 1HNMR (CD3OD, 400 MHz) δ 3.0 (s, 3H); 3.45 (br s, 2H); 3.62 (br s, 2H); 4.07 (br s, 4H).

1,2-Benzo-8-methyl-3,8-diazaspiro[4,5]decane-4-one 5

A solution of oxindole 4 (6.25 g, 47 mmol) in THF (500 ml) was cooled to −78 C and to it a solution of sodium hexamethyldisilazide (43 g, 235 mmol) in THF (300 ml) was added drop wise under N2 atmosphere. After stirring at −78 C for 45 min, N-methylbis (2-chloromethyl) amine hydrochloride (9 g, 47 mmol) was added, as a solid. The reaction mixture was stirred at −78 C for 1 h and at room temperature for 24 h. After quenching with H2O (90 ml), the mixture was extracted with ethyl acetate (3×100 ml). The organic extracts were washed with brine (25 ml), dried and the solvent removed in vacuo. Silica gel chromatography (5-50% MeOH/CH$_2$Cl$_2$, gradient) gave 6 g (57%) of 5 as a solid. 1HNMR (CD3OD, 400 MHz) δ 1.84 (m, 2H); 2.51 (m, 2H); 2.62 (s, 3H); 3.02 (m, 2H); 3.37 (m, 2H); 6.82 (d, 1H, J=7.68 Hz); 6.94 (t, 1H, J=7.58 Hz); 7.12 (t, 1H, J=7.7 Hz); 7.26 (d, 1H, J=9 Hz); 9.27 (br s, 1H).

5-Bromo-1,2-dihydro-2-oxospiro[3H-indole-3,4'-piperidine]-1'methyl 6

A solution of 1,2-Benzo-8-methyl-3,8-diazaspiro[4,5]decane-4-one (6.3 g, 29.1 mmol) in CH$_3$CN (100 ml) and MeOH (5 ml) was cooled to −5° C. and NBS (7.8 g, 44 mmol) was slowly added with stirring. The reaction mixture was stirred for 3.5 h at 0° C. Solvent was removed by vacuo. The residue was purified by silica gel chromatography (2-20% MeOH/CH$_2$Cl$_2$) to give 6 g as a solid. The solid compound was dissolved in ethyl acetate (600 ml) and washed with saturated aqueous NaHCO$_3$ solution, dried (Na$_2$SO$_4$). Evaporation of the solvent in vacuo gave 4.2 g (47%) of 6. $^1$HNMR (CD$_3$OD, 400 MHz) δ 7.51 (d, J=1.8 Hz, 1H), 7.35 (dd, J=1.9 and 8.2 Hz, 1H), 6.81 (d, J=8.2 Hz, 1H), 2.93 (m, 2H), 2.67 (m, 2H), 2.41 (s, 3H), 1.86 (m, 4H).

5-Bromo-1,2-dihydro-2-oxospiro[3H-indole-3,4'-piperidine]-1'-cyano 7

5-Bromo-1,2-dihydro-2-oxospiro[3H-indole-3,4'-piperidine]-1'-methyl 6 (4.6 g, 15.6 mmol) was dissolved in chloroform (700 ml) and treated with CNBr (22 g, 209.5 mmol) at room temperature. The mixture was heated to reflux for 24 h. The reaction mixture was cooled, diluted with methylene chloride (300 ml) and washed with 10% aqueous K$_2$CO$_3$ solution (2×100 ml). After the mixture was dried (Na$_2$SO$_4$) and concentrated, the residue was purified by silica gel chromatography (0-5% MeOH/CH$_2$Cl$_2$) to gave 7 as a solid 3.9 g (82%). 1HNMR (CDCl$_3$, 400 MHz) δ 7.52 (d, J=1.8 Hz, 1H), 7.37 (dd, J=1.8 and 8.2 Hz, 1H), 6.82 (d, J=8.2 Hz, 1H), 3.83 (m, 2H), 3.41 (m, 2H), 2.00 (m, 2H), 1.86 (m, 2H).

5-Bromo-spiro[indole-3,4'-piperidin]-2(1H)-one 2

5-Bromo-1,2-dihydro-2-oxospiro[3H-indole-3,4'-piperidine]-1'-cyano 7 (3.3 g, 10.8 mmol) was suspended in ethylene glycol (10 ml). The mixture was treated in NaOH (1.8 g, 45 mmol) and heated to 130° C. for 15 min. It was diluted with methylene chloride (500 ml) and washed with 10% aqueous K$_2$CO$_3$ (2×100 m). The organic layer was dried (Na$_2$SO$_4$) and concentrated and residue purified by silica gel chromatography (30% MeOH/CH$_2$Cl$_2$) to gave 2 as a light ceramic white solid 1.8 g (60%), mp 256-258° C. $^1$HNMR (DMSO-d$_6$, 400 MHz) δ 10.6 (br s, 1H, NH), 7.57 (d, J=1.84 Hz, 1H), 7.36 (d, J=8.2 Hz, 1H), 6.79 (d, J=8.2 Hz, 1H), 4.05 (br s, 1H, NH), 3.06 (m, 2H), 2.84 (m, 2H), 1.64 (m, 2H), 1.55 (m, 2H), $^{13}$C NMR (DMSO-d$_6$, 100 MHz) δ 180.93, 140.64, 137.98, 130.42, 126.75, 113.20, 111.45, 46.24, 40.92, 32.94. Anal. Calcd for C$_{12}$H$_{13}$BrN$_2$O: C, 51.26; H, 4.66; N, 9.9. Found: C, 50.87; H, 4.91; N, 9.67.

Example 17

1'-[(3-Methyl-1H-inden-2-yl)carbonyl]spiro[indene-1,4'-piperidine]

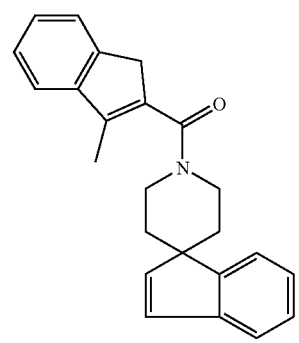

Amide coupling according to general procedure I:
Amine: Spiro[indene-1,4'-piperidine],
Acid: 3-Methyl-1H-indene-2-carboxylic acid,
ES-MS m/e (%): 342.5 (M+H$^+$).

Example 18

1'-(1H-Pyrrolo[2,3-b]pyridin-2-ylcarbonyl)spiro[indene-1,4'-piperidine]

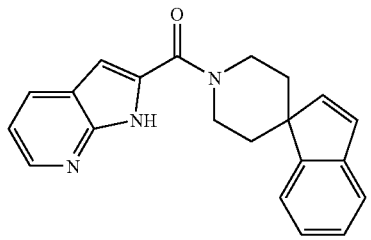

Amide coupling according to general procedure I:
Amine: Spiro[indene-1,4'-piperidine],
Acid: 1H-Pyrrolo[2,3-b]pyridine-2-carboxylic acid,
ES-MS m/e (%): 330.4 (M+H$^+$).

The invention claimed is:
1. A compound of the general formula (I)

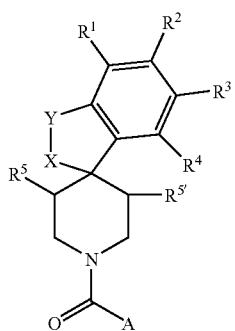

(I)

wherein
X—Y is CH═CH, or
X—Y is CH$_2$—CH$_2$;
A is selected from the group consisting of

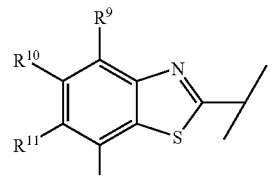
(a)

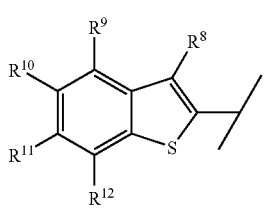
(b)

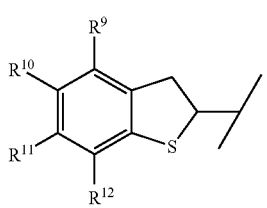
(c)

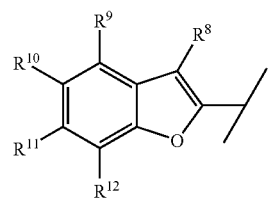
(d)

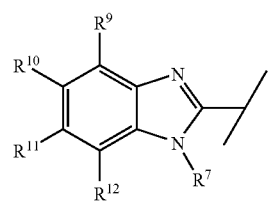
(e)

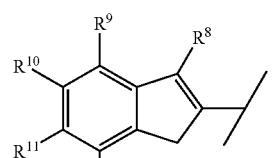
(f) and

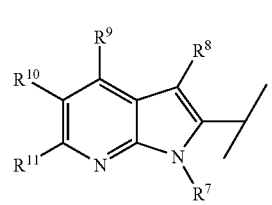
(g)

$R^1$, $R^2$, $R^3$ and $R^4$ are each independently
hydrogen,
halo,
C$_{1-6}$-alkyl, optionally substituted by OH
halo-C$_{1-6}$-alkyl,
C$_{1-6}$-alkoxy, optionally substituted by OH, or
halo-C$_{1-6}$alkoxy;
$R^5$ and $R^{5'}$ are each independently hydrogen or methyl;
$R^7$ is hydrogen,
C$_{1-6}$-alkyl, optionally substituted by CN or OH, or
—(C$_{1-6}$-alkylene)-C(O)—NR$^a$R$^b$;
$R^8$ is hydrogen,
C$_{1-6}$-alkyl,
C$_{1-6}$-alkoxy,
—(C$_{1-6}$-alkylene)-NR$^c$R$^d$,
—(C$_{1-6}$-alkylene)-C(O)R$^f$,
benzyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano, or
phenyl, optionally substituted by one or more halo, halo-C$_{1-6}$-alkyl, C$_{1-6}$-alkyl, C$_{1-6}$-alkoxy, halo-C$_{1-6}$-alkoxy, nitro, or cyano;
$R^9$ is hydrogen, halo, C$_{1-6}$-alkyl, or C$_{1-6}$-alkoxy;

$R^{10}$ is hydrogen, halo, $C_{1-6}$-alkyl, halo-$C_{1-6}$-alkyl, $C_{1-6}$-alkoxy, halo-$C_{1-6}$-alkoxy, or —O—$C_{2-10}$-alkenyl;

$R^{11}$ is hydrogen, halo, $C_{1-6}$-alkyl, or $C_{1-6}$-alkoxy;

or $R^{10}$ and $R^{11}$ are bound together to form a ring with the benzo moiety, wherein —$R^{10}$—$R^{11}$— is —O—(CH$_2$)$_n$—O— wherein n is 1 or 2;

$R^{12}$ is hydrogen,
- $C_{1-6}$-alkyl, optionally substituted by CN or OH,
- —($C_{1-6}$-alkylene)-NR$^g$R$^h$,
- —($C_{1-6}$-alkylene)-C(O)—NR$^i$R$^j$
- —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
- nitro,
- halo,
- cyano,
- $C_{1-6}$-alkoxy,
- halo-$C_{1-6}$-alkoxy,
- halo-$C_{1-6}$-alkyl,
- —($C_{1-6}$-alkylene)-C(O)R$^f$,
- phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
- —($C_{1-3}$-alkylene)-R$^m$,
  wherein R$^m$ is phenyl, a 5- to 6-membered heteroaryl, 4- to 6-membered heterocycloalkyl or 3 to 6-membered cycloalkyl,
  each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
- —NR$^n$R$^o$;

or $R^{11}$ and $R^{12}$ are bound together to form a ring with the benzo moiety, wherein
- —$R^{11}$—$R^{12}$— is —O—(CH$_2$)$_n$—C(O)—,
- —C(O)—(CH$_2$)$_n$—O—, or
- —O—(CH$_2$)$_n$—O— wherein n is 1 or 2;

R$^a$, R$^b$, R$^i$ and R$^j$ are each independently
- hydrogen,
- $C_{1-6}$-alkyl,
- —($C_{1-6}$-alkylene)-NR$^k$R$^l$,
  wherein R$^k$ and R$^l$ are each independently hydrogen or $C_{1-6}$-alkyl,
- or R$^a$ and R$^b$, or R$^i$ and R$^j$ together with the nitrogen to which they are bound form a five or six membered heterocycle comprising one or two heteroatoms selected from the group of nitrogen, oxygen and sulfur;

R$^c$, R$^d$, R$^g$, R$^h$, R$^n$ and R$^o$ are each independently
- hydrogen,
- $C_{1-6}$-alkyl,
- —C(O)R$^e$, or —S(O)$_2$R$^e$
  wherein R$^e$ is selected from the group of
  - hydrogen,
  - $C_{1-6}$-alkyl, and
  - phenyl, optionally substituted by one or more halo, halo-$C_{1-6}$-alkyl,
  - $C_{1-6}$-alkyl, $C_{1-6}$-alkoxy, halo-$C_{1-6}$-alkoxy, nitro, or cyano;
- or R$^c$ and R$^d$, or R$^n$ and R$^o$ together with the nitrogen to which they are bound form a five or six membered heterocycle comprising one or two heteroatoms selected from the group of nitrogen, oxygen and sulfur;

R$^f$ is selected from the group of
- hydrogen,
- $C_{1-6}$-alkyl,
- $C_{1-6}$-alkoxy; and
- phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

or a pharmaceutically acceptable salt thereof.

2. The compound of claim 1, wherein R$^a$ and R$^b$, R$^c$ and R$^d$, R$^i$ and R$^j$, or R$^n$ and R$^o$ together with the nitrogen to which they are bound form piperazine, 4-($C_{1-6}$-alkyl)-piperazine, 4-methylpiperazine, morpholine, piperidine or pyrrolidine.

3. The compound of claim 1, wherein R$^m$ is a 5- to 6-membered heteroaryl selected from the group consisting of pyridine, pyrimidine, pyrazine, pyridazine, imidazole, pyrazole, oxazole, and isoxazole.

4. The compound of claim 1, wherein R$^m$ is a 4- to 6-membered heterocycloalkyl selected from the group consisting of pyrrolidine, oxethane, tetraahydropyrane, piperidine, morpholine, and piperazine.

5. The compound of claim 1, wherein
$R^1$, $R^2$, $R^3$ and $R^4$ are each independently
- hydrogen,
- halo, or
- $C_{1-6}$-alkoxy, optionally substituted by OH.

6. The compound of claim 1, wherein
- $R^1$ is hydrogen;
- $R^2$ is hydrogen or $C_{1-6}$-alkoxy;
- $R^3$ is hydrogen, halo, or $C_{1-6}$-alkoxy, optionally substituted by OH; and
- $R^4$ is hydrogen.

7. The compound of claim 1, wherein $R^1$, $R^2$, $R^3$, and $R^4$ all are hydrogen.

8. The compound of claim 1, wherein one of $R^1$, $R^2$, $R^3$, and $R^4$ is halo and the others are hydrogen.

9. The compound of claim 1, wherein one of $R^1$, $R^2$, $R^3$, and $R^4$ is $C_{1-6}$-alkoxy, optionally substituted by OH.

10. The compound of claim 1, wherein $R^5$ and $R^{5'}$ are both hydrogen; are both methyl; or one is hydrogen and the other methyl.

11. The compound of claim 1, wherein
$R^7$ is hydrogen,
- $C_{1-6}$-alkyl, optionally substituted by CN or OH, or
- —($C_{1-6}$-alkylene)-C(O)—NR$^a$R$^b$,
  wherein R$^a$ and R$^b$ are each independently hydrogen or $C_{1-6}$-alkyl.

12. The compound of claim 1, wherein
$R^8$ is hydrogen,
- $C_{1-6}$-alkyl,
- $C_{1-6}$-alkoxy,
- —($C_{1-6}$-alkylene)-NR$^c$R$^d$,
  wherein R$^c$ and R$^d$ are each independently hydrogen, or
- —C(O)R$^e$, or —S(O)$_2$R$^e$
  wherein R$^e$ is selected from the group of
  - hydrogen,
  - $C_{1-6}$-alkyl, and
  - phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
- —($C_{1-6}$-alkylene)-C(O)R$^f$,
  wherein R$^f$ is selected from the group of
  - hydrogen,
  - $C_{1-6}$-alkyl,
  - $C_{1-6}$-alkoxy, and
  - phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
- benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano.

13. The compound of claim 1, wherein
$R^8$ is hydrogen, $C_{1-6}$-alkyl, or $C_{1-6}$-alkoxy.

14. The compound of claim 1, wherein
$R^9$ is hydrogen, or $C_{1-6}$-alkoxy.

15. The compound of claim 1, wherein
$R^{10}$ is hydrogen, halo, $C_{1-6}$-alkyl or $C_{1-6}$-alkoxy.

16. The compound of claim 1, wherein
$R^{11}$ is hydrogen, halo, $C_{1-6}$-alkyl, or $C_{1-6}$-alkoxy.

17. The compound of claim 1, wherein
$R^{11}$ is hydrogen.

18. The compound of claim 1, wherein
$R^{12}$ is hydrogen,
$C_{1-6}$-alkyl, optionally substituted by CN or OH,
—($C_{1-6}$-alkylene)-$NR^gR^h$, wherein $R^g$ and $R^h$ are each independently
hydrogen,
$C_{1-6}$-alkyl, or
—C(O)$R^e$, or —S(O)$_2R^e$, wherein $R^e$ is selected from
hydrogen,
$C_{1-6}$-alkyl, and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
—($C_{1-6}$-alkylene)-C(O)—$NR^iR^j$, wherein $R^i$ and $R^j$ are each independently
hydrogen,
$C_{1-6}$-alkyl, or
—($C_{1-6}$-alkylene)-$NR^kR^l$,
wherein $R^k$ and $R^l$ are each independently hydrogen or $C_{1-6}$-alkyl,
or $R^i$ and $R^j$ together with the nitrogen to which they are bound form a five or six membered heterocycle comprising one or two heteroatoms selected from the group of nitrogen, oxygen and sulfur;
—O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
nitro,
halo,
cyano,
$C_{1-6}$-alkoxy,
halo-$C_{1-6}$-alkoxy,
halo-$C_{1-6}$-alkyl,
—($C_{1-6}$-alkylene)-C(O)$R^f$, wherein $R^f$ is
$C_{1-6}$-alkyl,
$C_{1-6}$-alkoxy, or
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
—($C_{1-3}$-alkylene)-$R^m$,
wherein $R^m$ is phenyl, a 5- to 6-membered heteroaryl, 4- to 6-membered heterocycloalkyl or 3 to 6-membered cycloalkyl,
each optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
—$NR''R^o$,
wherein $R''$ and $R^o$ are each independently
hydrogen,
$C_{1-6}$-alkyl,
or $R''$ and $R^o$ together with the nitrogen to which they are bound form a five or six membered heterocycle comprising one or two heteroatoms selected from the group of nitrogen, oxygen and sulfur.

19. The compound of claim 1, wherein
$R^{12}$ is hydrogen,
$C_{1-6}$-alkyl, optionally substituted by CN or OH,
$C_{1-6}$-alkoxy, or
—$NR''R^o$,
wherein $R''$ and $R^o$ are each independently
hydrogen,
$C_{1-6}$-alkyl,
or $R''$ and $R^o$ together with the nitrogen to which they are bound form a five or six membered heterocycle comprising one or two heteroatoms selected from the group of nitrogen and oxygen.

20. The compound of claim 1, wherein
X—Y is CH=CH, and A is (f) or (g).

21. The compound of claim 1, which is selected from
1'-[(3-Methyl-1H-inden-2-yl)carbonyl]spiro[indene-1,4'-piperidine]; and
1'-(1H-Pyrrolo[2,3-b]pyridin-2-ylcarbonyl)spiro[indene-1,4'-piperidine].

22. A pharmaceutical composition comprising a therapeutically effective amount of a compound of formula (I)

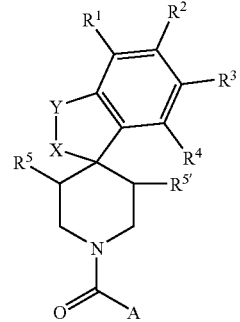

(I)

wherein
X—Y is CH=CH, or
X—Y is $CH_2$—$CH_2$;
A is selected from the group consisting of

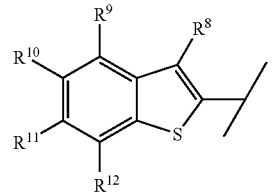

(a)

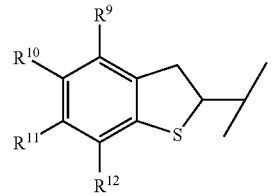

(b)

-continued (c)

[structure with R9, R10, R11, R12 on benzothiazole]

(d)

[structure with R8, R9, R10, R11, R12 on benzofuran]

(e)

[structure with R7, R8, R9, R10, R11, R12 on benzimidazole]

(f)

[structure with R8, R9, R10, R11, R12 on indene]

and (g)

[structure with R7, R8, R9, R10, R11 on pyrrolopyridine]

$R^1$, $R^2$, $R^3$ and $R^4$ are each independently
  hydrogen,
  halo,
  $C_{1-6}$-alkyl, optionally substituted by OH
  halo-$C_{1-6}$-alkyl,
  $C_{1-6}$-alkoxy, optionally substituted by OH, or
  halo-$C_{1-6}$alkoxy;
$R^5$ and $R^{5'}$ are each independently hydrogen or methyl;
$R^7$ is hydrogen,
  $C_{1-6}$-alkyl, optionally substituted by CN or OH, or
  —($C_{1-6}$-alkylene)-C(O)—$NR^aR^b$;
$R^8$ is hydrogen,
  $C_{1-6}$-alkyl,
  $C_{1-6}$-alkoxy,
  —($C_{1-6}$-alkylene)-$NR^cR^d$,
  —($C_{1-6}$-alkylene)-C(O)$R^f$,
  benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano, or
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

$R^9$ is hydrogen, halo, $C_{1-6}$-alkyl, or $C_{1-6}$-alkoxy;
$R^{10}$ is hydrogen, halo, $C_{1-6}$-alkyl, halo-$C_{1-6}$-alkyl, $C_{1-6}$-alkoxy, halo-$C_{1-6}$-alkoxy, or —O—$C_{2-10}$-alkenyl;
$R^{11}$ is hydrogen, halo, $C_{1-6}$-alkyl, or $C_{1-6}$-alkoxy;
or $R^{10}$ and $R^{11}$ are bound together to form a ring with the benzo moiety, wherein —$R^{10}$—$R^{11}$— is —O—($CH_2$)$_n$—O— wherein n is 1 or 2;
$R^{12}$ is hydrogen,
  $C_{1-6}$-alkyl, optionally substituted by CN or OH,
  —($C_{1-6}$-alkylene)-$NR^gR^h$,
  —($C_{1-6}$-alkylene)-C(O)—$NR^iR^j$
  —O-benzyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  nitro,
  halo,
  cyano,
  $C_{1-6}$-alkoxy,
  halo-$C_{1-6}$-alkoxy,
  halo-$C_{1-6}$-alkyl,
  —($C_{1-6}$-alkylene)-C(O)$R^f$,
  phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano,
  —($C_{1-3}$-alkylene)-$R^m$,
  wherein $R^m$ is phenyl, a 5- to 6-membered heteroaryl, 4- to 6-membered heterocycloalkyl or 3 to 6-membered cycloalkyl,
    each optionally substituted by one or more halo, halo-$C_{1-6}$-alkyl,
    $C_{1-6}$-alkyl, $C_{1-6}$-alkoxy, halo-$C_{1-6}$-alkoxy, nitro, or cyano, or
  —$NR^nR^o$;
or $R^{11}$ and $R^{12}$ are bound together to form a ring with the benzo moiety, wherein
  —$R^{11}$—$R^{12}$— is —O—($CH_2$)$_n$—C(O)—,
  —C(O)—($CH_2$)$_n$—O—, or
  —O—($CH_2$)$_n$—O— wherein n is 1 or 2;
$R^a$, $R^b$, $R^i$ and $R^j$ are each independently
  hydrogen,
  $C_{1-6}$-alkyl, or
  —($C_{1-6}$-alkylene)-$NR^kR^l$,
  wherein $R^k$ and $R^l$ are each independently hydrogen or $C_{1-6}$-alkyl,
  or $R^a$ and $R^b$, or $R^i$ and $R^j$ together with the nitrogen to which they are bound form a five or six membered heterocycle comprising one or two heteroatoms selected from the group of nitrogen, oxygen and sulfur;
$R^c$, $R^d$, $R^g$, $R^h$, $R^n$ and $R^o$ are each independently
  hydrogen,
  $C_{1-6}$-alkyl, or
  —C(O)$R^e$, or —S(O)$_2R^e$
  wherein $R^e$ is selected from the group of
    hydrogen,
    $C_{1-6}$-alkyl, and phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;
  or $R^c$ and $R^d$, or $R^n$ and $R^o$ together with the nitrogen to which they are bound form a five or six membered heterocycle comprising one or two heteroatoms selected from the group of nitrogen, oxygen and sulfur;

$R^f$ is selected from the group of
hydrogen,
$C_{1-6}$-alkyl,
$C_{1-6}$-alkoxy; and
phenyl, optionally substituted by one or more halo, halo-$C_{1-6}$-alkyl, $C_{1-6}$-alkyl, $C_{1-6}$-alkoxy, halo-$C_{1-6}$-alkoxy, nitro, or cyano;

or a pharmaceutically acceptable salt thereof and a pharmaceutically acceptable carrier.

* * * * *